United States Patent [19]

Shepherd et al.

[11] Patent Number: 4,489,094

[45] Date of Patent: Dec. 18, 1984

[54] ARYLALKYLAMINOBENZOIC ACIDS

[75] Inventors: Robert G. Shepherd, Selbyville, Del.; Janis Upeslacis, Pomona, N.Y.

[73] Assignee: American Cyanamid Company, Stamford, Conn.

[21] Appl. No.: 492,095

[22] Filed: May 6, 1983

[51] Int. Cl.³ ................. A61K 31/245; A61K 31/195; C07C 101/60; C07C 101/62
[52] U.S. Cl. ..................................... 424/310; 424/319; 560/36; 562/441
[58] Field of Search ...................... 560/19, 20, 21, 36; 562/433, 441, 457, 458; 424/310

[56] References Cited

U.S. PATENT DOCUMENTS 4,143,151  3/1979  Wagner et al. ..................... 424/310

FOREIGN PATENT DOCUMENTS 2062621  5/1981  United Kingdom ................. 560/19

*Primary Examiner*—Natalie Trousof
*Assistant Examiner*—Bruce D. Gray
*Attorney, Agent, or Firm*—Edward A. Conroy, Jr.

[57] ABSTRACT

This disclosure describes novel [Bis(phenyl or substituted phenyl)alkyl]amino benzoic acids, esters, and derivatives thereof. These compounds are useful pharmaceutical agents for ameliorating atherosclerosis by inhibiting the formation and development of atherosclerotic lesions in the arterial walls of mammals.

11 Claims, No Drawings

ARYLALKYLAMINOBENZOIC ACIDS

BACKGROUND OF THE INVENTION

This invention relates to new organic compounds useful as pharmaceutical agents. The novel compounds of the present invention are antiatherosclerotic agents capable of ameliorating atherosclerosis by counteracting the formation or development of atheromatous lesions in the arterial wall of mammals. The invention also relates to the chemical synthesis of the novel compounds disclosed herein. In addition, the invention pertains to novel pharmaceutical compositions for the utilization of these compounds in the treatment of disease in mammals. Further, the invention contemplates methods for treating atherosclerosis in a manner designed to prevent, arrest, or reverse the course of the disease.

Atherosclerosis is a form of arteriosclerosis characterized by lipid accumulation in and thickening of the arterial walls of both medium- and large-sized arteries. Arterial walls are thereby weakened, and the elasticity and effective internal size of the artery is decreased. Atherosclerosis is the most common cause of coronary artery disease and is of great medical importance since the occlusion of medium- and large-sized arteries diminishes the supply of blood to vital organs such as the heart muscles and the brain. The sequelae to atherosclerosis include ischemic heart disease, heart failure, life-threatening arrythmias, senility, and stroke.

The fact that cholesterol is a major component of atherosclerotic lesions or plagues has been known for more than 100 years. Various researchers have studied the role of cholesterol in the lesion formation and development and also, more importantly, whether lesion formation can be prevented or lesion development arrested or reversed. Atheromatous lesions have now been shown [Adams, et al., Atherosclerosis, 13, 429 (1974)] to contain a greater quantity of esterified as opposed to unesterified cholesterol than the surrounding undiseased arterial wall. The intracellular esterification of cholesterol with fatty acids is catalyzed by the enzyme "Fatty acyl CoA: cholesterol acyl transferase" or ACAT, and the accumulation and storage of cholesterol esters in the arterial wall is associated with increased levels of this enzyme [Hashimoto and Dayton, Atherosclerosis, 28, 447 (1977)]. In addition, cholesterol esters are removed from cells at a slower rate than unesterified cholesterol [Bonjers and Bjorkerud, Atherosclerosis, 15, 273 (1972) and 22, 379 (1975)]. Thus, inhibition of the ACAT enzyme would diminish the rate of cholesterol esterification, decrease the accumulation and storage of cholesterol esters in the arterial wall, and prevent or inhibit the formation and development of atheromatous lesions. The compounds of the present invention are very potent inhibitors of the ACAT enzyme. Thus, these compounds are useful for controlling and normalizing the cholesterol ester content of mammalian arterial walls. In contrast to the serum hypocholesterolemic agents which are well known in the art to merely lower cholesterol in the blood stream, the compounds of this invention decrease the accumulation and storage of cholesterol in the arterial walls of mammals. Further, the compounds of this invention inhibit the formation or development of atherosclerotic lesions in mammels. The exact mechanism by which these compounds exhibit this antiatherosclerotic activity is not known, and the invention should not be construed as limited to any particular mechanism of antiatherosclerotic action.

SUMMARY OF THE INVENTION

This invention relates to new organic compounds and more particularly is concerned with [bis(phenyl or substituted phenyl)alkyl]aminobenzoic acids, esters, and derivatives thereof of the formula:

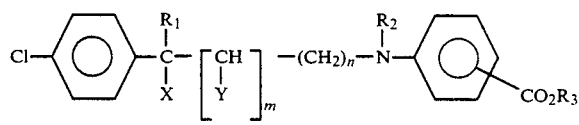

wherein $R_1$ is selected from the group consisting of phenyl, chlorophenyl, fluorophenyl, and when $R_2$ is not hydrogen, also from the group consisting of hydrogen and $C_1$-$C_4$ alkyl; $R_2$ is selected from the group consisting of hydrogen, $C_1$-$C_4$ alkyl, and

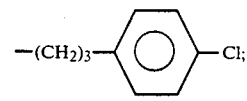

$R_3$ is selected from the group consisting of hydrogen, $C_1$-$C_4$ alkyl, alkali metal, and alkaline earth metal; X and Y may each be hydrogen or taken together may be a carbon-to-carbon bond; m is an integer 0 or 1; and n is an integer 0 or 1.

Preferred embodiments of the invention relate to those compounds wherein $R_1$ is p-chlorophenyl and $R_2$ is hydrogen. Of course, the more preferred compounds are those wherein both n and m are the integer 1. Of the latter group, the most preferred are those compounds in which the group —$COOR_3$ is para to the amino substituent on the benzene ring.

Representative specific embodiments include, for example, ethyl 4-[[3,3-bis(p-chlorophenyl)propyl]amino]benzoate; 4-[[3,3-bis(p-chlorophenyl)propyl]amino]benzoic acid; ethyl 4-[[3,3-bis(p-chlorophenyl)allyl]amino]benzoate; 4-[[3,3-bis(p-chlorophenyl)allyl]amino]benzoic acid; 4-[[3,3-bis-(p-chlorophenyl)propyl]amino]benzoate; and 4-[[3,3-bis(p-chlorophenyl)alkyl]amino]benzoate.

This invention also relates to a method of reducing the cholesterol content of the arterial walls of mammals which comprises administering to said mammal an effective amount of a compound as recited above.

This invention further relates to a method of inhibiting atherosclerotic lesion development in mammals which comprises administering to said mammal an effective amount of a compound as recited above.

This invention still further relates to a pharmaceutical composition which comprises an effective antiatherosclerotic amount of a compound as recited above in association with a pharmaceutically-acceptable carrier.

Finally, this invention relates to a process for preparing compounds as recited above which comprises reacting a compound of the formula:

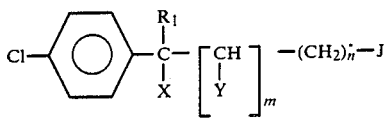

with an aniline of the formula:

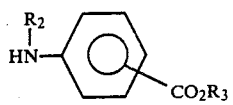

wherein $R_1$, $R_2$, $R_3$, X, Y, m, and n are as defined above, and J is selected from the group consisting of halo, alkylsulfonyloxy, and arylsulfonyloxy.

DETAILED DESCRIPTION OF THE INVENTION

Many of the compounds of this invention are prepared by reactions of diarylalkyl- and diarylalkenyl-halides, alkylsulfonate esters, or arylsulfonate esters with aminobenzoate esters. For example, reaction of the methane-sulfonate ester of 3,3-(p-chlorophenyl)-propanol with ethyl 4-aminobenzoate yields ethyl 4-[3,3-(p-chlorophenyl)propylamino]benzoate. Alkaline hydrolysis in the presence of sodium hydroxide of this benzoate ester affords 4-[3,3-(p-chlorophenyl)-propylamino]benzoic acid which may be isolated as such by acidification or as sodium 4-[3,3-(p-chlorophenyl)propylamino]benzoate by evaporation.

The compounds of the present invention are generally obtained as crystalline solids having characteristic melting points and spectra. They are appreciably soluble in many organic solvents but are generally less soluble in water. Those compounds which are carboxylic acids may be converted to their alkali metal and alkaline earth salts by treatment with appropriate metal hydroxides, and these salts exhibit increased water solubility.

The preparation and properties of the compounds of this invention will be described in greater detail in conjunction with the specific examples shown below.

The compounds of the present invention were tested for their ability to inhibit the enzymatic esterification of cholesterol according to the following procedure:

Rat adrenals were homogenized in 0.2M monobasic potassium phosphate buffer, pH 7.4, and centrifuged at 1,000 times gravity for 15 minutes at 5° C. The supernatant, containing the microsomal fraction, served as the source of the cholesterol-esterifying enzyme, fatty acyl CoA: cholesterol acyl transferase (ACAT). A mixture comprising 50 parts of adrenal supernatant, 10 parts of albumin (BSA) (50 mg./m.), 20 parts of oleoyl CoA ($^{14}$C-0.4 μCi), 3 parts of test compound, and 500 parts of buffer was pre-incubated at 37° C. for 10 minutes. After treatment with 20 parts of oleoyl CoA ($^{14}$C-0.4 μCi), the mixture was incubated at 37° C. for 10 minutes. A control mixture, omitting the test compound, was prepared and treated in the same manner. The lipids from the incubation mixture were extracted into an organic solvent and separated by thin-layer chromatography. The cholesterol ester fraction was counted in a scintillation counter. This procedure is a modification of that described by Hashimoto, et al. Life Scie., 12 (Part II), 1-12 (1973).

The results of this test on representative compounds of this invention appear in Table I. The final concentration of the test compound was 5.2 μg./ml., and effectiveness of the compound is expressed as percent inhibition of the ACAT enzyme compared to control values.

TABLE I

| COMPOUND | % INHIBITION |
| --- | --- |
| 4-[[3-(p-Chlorophenyl)propyl]methylamino]benzoic acid | 24 |
| 4-[[3-(p-Chlorophenyl)propyl]methylamino]benzoic acid, ethyl ester | 53 |
| 4-[[3-(p-Chlorophenyl)propyl]ethylamino]benzoic acid, ethyl ester | 48 |
| 4-[[3-(p-Chlorophenyl)propyl]ethylamino]benzoic acid | 33 |
| 4[[2,2-Bis(p-chlorophenyl)ethyl]amino]benzoic acid | 19 |
| 4-[[3,3-Bis(p-chlorophenyl)propyl]amino]benzoic acid, ethyl ester | 89 |
| 4-[[3,3-Bis(p-chlorophenyl)propyl]amino]benzoic acid | 21 |
| 4-[Bis[3-(p-chlorophenyl)propyl]amino]benzoic acid | 33 |
| 4-[[3,3-Bis(p-chlorophenyl)allyl]amino]benzoic acid, ethyl ester | 81 |
| 4-[[3,3-Bis(p-chlorophenyl)allyl]amino]benzoic acid | 46 |
| 4-[[Bis(p-chlorophenyl)methyl]amino]benzoic acid, ethyl ester | 55 |
| 4-[[(p-chlorophenyl)methyl]amino]benzoic acid | 6 |

When the compounds are employed for the above utility, they may be combined with one or more pharmaceutically-acceptable carriers, e.g., solvents, diluents, and the like, and may be administered orally in such forms as tablets, capsules, dispersible powders, granules, suspensions containing, for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed for the reduction of cholesterol ester content in the arterial walls of a mammal may vary depending on the particular compound employed, the mode of administration, and the severity of the condition being treated. In general, however, satisfactory results are obtained when the compounds of the invention are administered at a daily dosage of from about 2 milligrams to about 500 milligrams per kilogram of animal body weight, preferably given in divided doses two to four times a day, or in sustained release form. For most large mammals, the total daily dosage is from about 100 milligrams to about 5,000 milligrams, preferably from about 100 milligrams to 2,000 milligrams. Dosage forms suitble for internal use comprise about 25 to 2,500 milligrams of the active compound in intimate admixture with a solid or liquid pharmaceutically-acceptable carrier. This dosage regimen may be adjusted to provide the optimal therapeutic response. For example, several divided doses may be administered daily, or the dose may be proportionally reduced as indicated by the exigencies of the therapeutic situation.

A decided practical advantage is that these active compounds may be administered orally as well as by intravenous, intramuscular, or subcutaneous routes, if necessary. Solid carriers include starch, lactose, and kaolin, while liquid carriers include sterile water, polyethylene glycols, and edible oils such as corn, peanut and sesame, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT, and BHA.

The preferred pharmaceutical compositions from the stand-point of ease of preparation and administration are solid compositions, particularly tablets and hard-filled or liquid-filled capsules. Oral administration of Compound I is preferred.

These active compounds may also be administered parenterally or intraperitoneally. Solutions or suspensions of these active compounds as a free base or pharmacologically-acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

EXAMPLE 1

4-[[3-(p-Chlorophenyl)propyl]methylamino]benzoic acid, ethyl ester

A 550 ml. portion of 1M diborane in tetrahydrofuran is placed in a flask under nitrogen and cooled in an ice bath. An 82.5 g. portion of 3-(p-chlorophenyl)propionic acid in 250 ml. of dry tetrahydrofuran is added dropwise over a period of one hour. The cooling bath is removed, and the mixture is allowed to stand overnight and is then poured slowly into 1.5 liters of ice water with swirling. The mixture is extracted with three 500 ml. portions of ether. The ether extracts are combined, washed with 250 ml. of brine, dried over magnesium sulfate, and evaporated, yielding 72.9 g. of 3-(p-chlorophenyl)propanol as an oil.

This oil is combined with 86.4 g. of triethyl amine and 1.5 liters of dry dichloromethane and cooled to −10° C. in an ethanol-dry ice bath. A 54.2 g. portion of methylsulfonyl chloride is added dropwise over a period of ½ hour. The mixture is allowed to warm to room temperature over ½ hour, and the dichloromethane solution is extracted with one liter of each of the following ice-cold solutions: water, 10% hydrochloric acid, saturated aqueous sodium bicarbonate, and brine. The dichloromethane extract is then dried over anhydrous magnesium sulfate and evaporated at reduced pressure, giving 105 g. of 3-(p-chlorophenyl)propyl mesylate as an orange oil.

The above mesylate (105 g.) is placed in a flask and 150 g. of ethyl p-aminobenzoate and 300 ml. of hexamethylphosphortriamide are added. The solution is warmed to 125° C. under nitrogen and stirred for 16 hours, then cooled and poured into 500 ml. of water. The solid is collected, washed with 150 ml. of 50% ethanol, then crystallized from 900 ml. of a mixture of acetonitrile and ethanol (1:1) giving 111.8 g. of ethyl 4-[3-(p-chlorophenyl)propylamino]benzoate.

A mixture of 1.0 g. of ethyl 4-[3-(p-chlorophenyl)-propylamino]benzoate, 20 ml. of dry dichloromethane and 2.5 ml. of methane sulfonyl fluoride is stirred for 18 hours, then refluxed for 3 hours. The solution is poured into 30 ml. of water and adjusted to pH 10 with 10N sodium hydroxide. The dichloromethane layer is separated and saved. The aqueous layer is extracted with two 20 ml. portions of dichloromethane. The organic layers are combined, washed with 10 ml. of water, dried over anhydrous magnesium sulfate, and evaporated to yield 1.80 g. of the desired product as a light yellow oil.

EXAMPLE 2

4-[[3-(p-Chlorophenyl)propyl]methylamino]benzoic acid

A 1.80 g. portion of 4-[[3-(p-chlorophenyl)propyl]-methylamino]benzoic acid, ethyl ester is dissolved in 15 ml. of 95% ethanol. A 1 g. portion of potassium hydroxide is added, and the mixture is refluxed overnight. The solution is poured into 30 ml. of water, the pH is adjusted to 6 using 37% hydrochloric acid, and the solid is collected and dried. This solid is dissolved in benzene, filtered, and evaporated, giving 750 mg. of the desired product.

EXAMPLE 3

4-[[3-(p-Chlorophenyl)propyl]ethylamino]benzoic acid, ethyl ester

A mixture of 1 g. of ethyl 4-[3-(p-chlorophenyl)-propylamino]benzoate and 2.37 g. of diethyl sulfate is stirred at 130° C. for 3 hours. The mixture is then diluted with 10 ml. of dichloromethane and 10 ml. of water and adjusted to pH 11 with 10N sodium hydroxide. The dichloromethane layer is drawn off and saved. The aqueous layer is extracted with two 10 ml. portions of dichloromethane. The organic layers are combined, washed with 10 ml. of water, dried over anhydrous magnesium sulfate and evaported to an oil. This oil is chromatographed on a silica gel column, eluting with chloroform:hexane (1:3) giving a colorless liquid which is distilled, giving the desired product as a liquid, boiling point 160° C. (14 mm.).

EXAMPLE 4

4-[[3-(p-Chlorophenyl)propyl]ethylamino]benzoic acid

A 2.0 g. portion of 4-[[3-(p-chlorophenyl)propyl]e-thylamino]benzoic acid, ethyl ester is dissolved in 50 ml. of 95% ethanol. A 4.0 g. portion of potassium hydroxide is added, and the solution is refluxed overnight. The solution is filtered, then diluted with 100 ml. of water, and adjusted to pH 6.5 with 37% hydrochloric acid. This mixture is extracted with two 50 ml. portions of dichloromethane, which are combined, washed with 50 ml. of water, and evaporated to an oil. This oil is chromatographed on a silica gel column, eluting with chloroform, followed by 10% ethyl acetate in chloroform. The ethyl acetate-chloroform eluate is crystallized from ethanol, giving 700 mg. of the desired product as a tan solid.

EXAMPLE 5

4-[[3,3-Bis(p-chlorophenyl)propyl]amino]benzoic acid, ethyl ester

A 100 g. portion of 30-mesh zinc is kept in a mixture of concentrated sulfuric acid and concentrated nitric acid at 100° C. for one hour. The hot acid is decanted and 300 ml. of water are added to the zinc. When the reaction subsides, the zinc is collected by filtration, washed with 500 ml. of water and 100 ml. of acetone, and dried in vacuo.

A mixture of 100.4 g. of 4,4'-dichlorobenzophenone, 133.6 g. of ethyl bromoacetate, 300 ml. of toluene, and 400 ml. of benzene is brought to reflux, and 100 ml. of the solution is distilled off. When the solution is thoroughly dried, 64.5 g. of activated zinc are added slowly, then crystals of iodine are added to initiate the reaction. The vigorous reflux which results is controlled by placing the flask in an ice-water bath. The procedure is repeated until the reaction no longer sustains reflux, then the mixture is heated to reflux for 2 hours. The hot solution is poured with stirring into a solution of 200 ml. of 20% sulfuric acid and 500 g. of ice. After the ice melts, the layers are separated. The organic layer is dried over anhydrous magnesium sulfate and saved. The aqueous layer is extracted with 200 ml. of benzene. The benzene extract is dried, combined with the original organic layer and evaporated, giving 216 g. of 3,3-bis(p-chlorophenyl)hydracrylic acid, ethyl ester.

A 221 g. portion of the 3,3-bis(p-chlorophenyl)hydracrylic acid, ethyl ester is dissolved in one liter of 95% ethanol. To this is added 100 ml. of water and 44 g. of potassium hydroxide. The solution is stirred at reflux for 2½ hours, cooled, and poured into 3 liters of water. The mixture is filtered, adjusted to pH 1 with 300 ml. of 20% sulfuric acid, and the precipitate is collected. This solid is crystallized from 600 ml. of toluene giving 53.69 g. of bis-$\beta,\beta$-(p-chlorophenyl)acrylic acid as tan crystals.

A solution of 48.52 g. of bis-$\beta,\beta$-(p-chlorophenyl)acrylic acid and 60 g. of sulfonyl chloride in 25 ml. of benzene is stirred at reflux for 4 hours, then cooled and evaporated. The residue is evaporated three times from benzene, giving 41.8 g. of bis-$\beta,\beta$-(p-chlorophenyl)acryloyl chloride as a solid. The entire amount of this solid is dissolved in 250 ml. of dichloromethane, and to this solution is added slowly a mixture of 24.3 g. of ethyl 4-aminobenzoate and 14.8 g. of triethylamine in 250 ml. of dichloromethane. The reaction is stirred for 2 hours, then refluxed for 1 hour, and cooled. The mixture is washed with 300 ml. of 10% hydrochloric acid. The acid wash is in turn washed with 100 ml. of dichloromethane. The organic layers are combined, concentrated to a solid, then boiled in 250 ml. of ethanol and 200 ml. of chloroform. The solution is filtered, boiled down to 250 ml., and the solid is collected and washed with 400 ml. of ethanol, giving 33.74 g. of 4-[3,3-bis(p-chlorophenyl)acrylamide]benzoic acid, ethyl ester.

A mixture of 30.2 g. of 4-[3,3-bis(p-chlorophenyl)acrylamido]benzoic acid, ethyl ester and 500 mg. of 10% palladium on carbon in 130 l ml. of dry tetrahydrofuran is hydrogenated in a Parr apparatus until hydrogen uptake is complete. The mixture is filtered, and the filtrate is evaporated giving an oil which is crystallized from isopropanol, giving 25.97 g. of 4-[3,3-bis(p-chlorophenyl)propionamido]benzoic acid, ethyl ester.

A 60 ml. portion of sodium borohydride in tetrahydrofuran is added to flask and cooled in an ice-water bath. A solution of 14.26 g. of 4-[3,3-bis(p-chlorophenyl)propionamido]benzoic acid, ethyl ester in 100 ml. of tetrahydrofuran is added dropwise. The solution is then refluxed for 2 hours, cooled, and 50 ml. of hydrochloric acid in ethanol are added. The mixture is refluxed for 1 hour, cooled, and evaporated. The residue is boiled with two 250 ml. portions of hexane, then with two 250 ml. portions of heptane, and then concentrated to a solid. This solid is crystallized from 200 ml. of methyl cyclohexane, giving 8.29 g. of the desired product as yellow crystals, m.p. 112°–117° C.

EXAMPLE 6

4-[[3,3-Bis(p-chlorophenyl)propyl]amino]benzoic acid

A mixture of 4.25 g. of p-[[3,3-bis(p-chlorophenyl)propyl]amino]benzoic acid, ethyl ester, 2.85 g. of potassium hydroxide, and 50 ml. of 95% ethanol is heated at 75° C. for 26 hours, cooled, diluted with 150 ml. of water, and adjusted to pH 5 with 37% hydrochloric acid. The solid is collected, dried, and crystallized twice from isopropanol, giving 2.88 g. of the desired product as tan crystals, m.p. 213°–215° C.

EXAMPLE 7

4-[[3,3-Bis(p-chlorophenyl)allyl]amino]benzoic acid, ethyl ester

To 36 g. of sodium hydride (50% in mineral oil) is added 350 ml. of hexane under argon. The hexane is then decanted, and the sodium hydride is suspended in 1.8 liters of 1,2-dimethoxyethane and cooled in an ice bath. To this mixture is added 165 g. of triethylphosphonoacetate over 30 minutes, maintaining the temperature below 20° C. The mixture is stirred 15 minutes, then 185 g. of 4,4'-dichlorobenzophenone are added portionwise over 15 minutes with continued cooling. The mixture is then stirred at room temperature for 24 hours, diluted with 2.3 liters of hexane and stirred for 30 minutes. The supernatant is decanted, filtered, and dried in vacuo, then concentrated and cooled. The solid is dissolved in hot hexane, treated with charcoal, filtered, diluted to 1 liter with hexane, and refrigerated overnight. The solid is collected and washed with hexane, giving 252 g. of bis-$\beta,\beta$-(p-chlorophenyl)acrylic acid, ethyl ester.

To a solution of 10.0 g. of bis-$\beta,\beta$-(p-chlorophenyl)acrylic acid, ethyl ester in 130 ml. of ether under nitrogen, cooled in a dry ice-acetonitrile bath, is added portionwise 900 mg. of lithium aluminum hydride. The temperature is maintained below −29° C. during addition and is stirred at this temperature for 2½ hours. A 0.9 ml. portion of water, 0.9 ml. of 15% sodium hydroxide, and then 2.70 ml. of water are sequentially added with vigorous stirring, and the mixture is filtered. The ether filtrate is dried over magnesium sulfate and concentrated to an oil. The oil is distilled in a Kugelrohr apparatus, collecting the fraction that boils at 175° C., affording 3,3-bis(p-chlorophenyl)-2-propen-1-ol as a yellow oil.

A 12.04 g. portion of 3,3-bis(p-chlorophenyl)-2-propen-1-ol, prepared as described above, is dissolved in dichloromethane and chromatographed on a silica gel column, eluting with dichloromethane. Fractions 7–11 are combined and concentrated at 35° C. to an oil, which is solidified by refrigeration and dried, giving 5.5 g. of the purified product.

To a solution of 3.0 g. of the purified 3,3-bis(p-chlorophenyl)-2-propen-1-ol, 50 ml. of ether, and 1.7 g. of triethylamine, cooled to −30° C., is added 1.36 g. of methane sulfonyl chloride. This mixture is stirred at −30° C. for 30 minutes, then allowed to warm to room temperature, and filtered. The solid is washed with ether. Both the solid and the ether wash are added to a solution of 3.6 g. of ethyl p-aminobenzoate in 50 ml. of ether. A 50 ml. portion of dichloromethane is added and the mixture is stirred overnight. The mixture is filtered and washed with dichloromethane. The organic layer is washed three times with water, once with saturated sodium chloride solution, dried over magnesium sulfate, and filtered. The filtrate is concentrated to an oil, then triturated with ether, giving a solid which is collected, dissolved in dichloromethane, and chromatographed, eluting with 30% hexane in dichloromethane and taking 50 ml. fractions. Fractions 6–9 are combined and concentrated to a solid which is dissolved in 500 ml. of ether and concentrated, giving 0.96 g. of the desired product as a white solid.

EXAMPLE 8

4-[[3,3-Bis(p-chlorophenyl)allyl]amino]benzoic acid

A suspension of 1.3 g. of p-[[3,3-bis(p-chlorophenyl)allyl]amino]benzoic acid, ethyl ester, 40 ml. of ethanol, and 4.6 ml. of 1N sodium hydroxide is heated at reflux for 28 hours, cooled, and then diluted with an equal volume of water. A 0.26 ml. portion of glacial acetic acid is added, and the mixture is cooled in ice. The solid is collected, washed with water, and recrystallized from absolute ethanol, giving 600 mg. of the desired product, m.p. 231°–235° C.

EXAMPLE 9

4-[Bis[3-(p-chlorophenyl)propyl]amino]benzoic acid

A suspension of 50 g. of p-chlorocinnamic acid and 1 g. of 10% palladium on carbon in 200 ml. of tetrahydrofuran is hydrogenated in a Parr apparatus until the uptake of hydrogen is complete. The mixture is then filtered and evaporated, giving 50.42 g. of 3-(p-chlorophenyl)propionic acid.

A 1.5 liter portion of 1M diborane in tetrahydrofuran is placed in a flask, under argon, and cooled in an icewater bath. A solution of 171.8 g. of 3-(p-chlorophenyl)propionic acid (prepared as described above) in 500 ml. of dry tetrahydrofuran is added slowly with stirring. The bath is removed, and the mixture is stirred overnight at room temperature. The solution is poured into 2 liters of stirred ice water and then extracted with three 650 ml. portions of ether. The ether extracts are combined, washed with 500 ml. of water, dried over magnesium sulfate, and condensed to an oil. This oil is distilled in a Kugelrohr apparatus, collecting the fraction with a boiling range of 100°–115° C. (140 mm.), giving 128.2 g. of 3-(p-chlorophenyl)propanol as a colorless liquid.

A solution of 128 g. of 3-(p-chlorophenyl)propanol and 114 g. of triethylamine in 1.5 liters of dichloromethane is cooled to −10° C. A 9.5 g. portion of methane sulfonyl chloride is added dropwise with stirring, and the temperature is maitained at −10° C. The bath is removed, and the mixture is stirred for one hour. The dichloromethane is extracted with 400 ml. each of ice cold water, 10% hydrochloric acid, saturated sodium bicarbonate solution, and brine. The dichloromethane layer is then dried and evaporated, giving 188 g. of 3-(p-chlorophenyl)propyl mesylate.

A solution of 167.7 g. of 3-(p-chlorophenyl)propyl mesylate and 223 g. of ethyl 4-aminobenzoate in 350 ml. of hexamethylphosphortriamide is stirred at 115° C. for 16 hours. The warm solution is slowly poured into 700 ml. of water with stirring. The solid is collected, washed with water, dried, and crystallized twice from 1.2 liters of ethanol, giving 167.3 g. of 4-[[3-(p-chlorophenyl)propyl]amino]benzoic acid, ethyl ester.

A solution of 8.6 g. of 3-(p-chlorophenyl)propyl mesylate and 10 g. of 4-[[3-(p-chlorophenyl)propyl]amino]benzoic acid, ethyl ester in 50 ml. of hexamethylphosphortriamide is stirred overnight at 120° C. and then for 14 days with the periodic addition of a total of 15.2 g. of potassium carbonate. The solution is cooled, diluted with 100 ml. of water, and extracted with three 100 ml. portions of ether. The ether extracts are combined, washed with 100 ml. of water, dried over magnesium sulfate, and condensed to a solid. This solid is dissolved in 300 ml. of ethanol, filtered, condensed, and chromatographed on silica gel, giving 5.64 g. of 4-[bis[3-(p-chlorophenyl)propyl]amino]benzoic acid, ethyl ester.

A solution of 5.6 g. of 4-[bis[3-(p-chlorophenyl)propyl]amino]benzoic acid, ethyl ester and 3 g. of 85% potassium hydroxide in 50 ml. of ethanol is stirred at 75° C. for 4 hours, cooled, diluted with 100 ml. of water, and adjusted to pH 6.0 with 37% hydrochloric acid. The solution is extracted with two 150 ml. portions of ether. The ether extracts are combined, washed with 100 ml. of water, then 100 ml. of brine, dried over magnesium sulfate, and evaporated to an orange solid. This solid is recrystallized twice from 50 ml. of acetonitrile, giving 1.39 g. of the desired product, m.p. 128°–131° C.

EXAMPLE 10

4-[[2,2-Bis(p-chlorophenyl)ethyl]amino]benzoic acid

A mixture of 49.5 g. of 1,1'-(2,2,2-Trichloroethylidene)bis(p-chlorobenzene), 400 ml. of diethylene glycol, and a solution of 6.3 g. of potassium hydroxide in 35 ml. of water is refluxed at 135° C. for 6 hours, cooled, and slowly poured into 1 liter of cold water with stirring. The mixture is filtered, the filtrate is warmed to 90° C., and 2 g. of charcoal are added. After 10 minutes, the charcoal is filtered off, and the filtrate is made acidic with 55 ml. of concentrated sulfuric acid. This solution is refrigerated for 6 hours, then the solid is collected, dried, and recrystallized from ethanol:water (100:75), giving 28.0 g. of bis(p-chlorophenyl)acetic acid.

To a stirred mixture of 23.55 g. of the above acid in 250 ml. of benzene is added dropwise 33.1 g. of sulfonyl chloride. The mixture is refluxed 5 hours, the solvent evaporated, and the residue evaporated from three 250 ml. portions of benzene, giving 26.06 g. of bis(p-chlorophenyl)acetyl chloride as a yellow oil. To this oil is added a solution of 27.7 g. of ethyl 4-aminobenzoate in 250 ml. of benzene. A 250 ml. portion of dichloromethane is added, and the mixture is stirred overnight. The mixture is filtered, and the filtrate is washed with 200 ml. each of 10% hydrochloric acid, saturated sodium bicarbonate solution, water, and brine, dried over magnesium sulfate, and evaporated to a solid. This solid is crystallized twice from 200 ml. of ethanol, giving 25.76 g. of 4-[2,2-bis(p-chlorophenyl)acetamido]benzoic acid, ethyl ester.

To a 55 ml. portion of 1M borane in tetrahydrofuran under nitrogen is added with stirring a solution of 12.0 g. of 4-[2,2-bis(p-chlorophenyl)acetamido]benzoic acid, ethyl ester in 100 ml. of dry tetrahydrofuran. The mixture is refluxed 2½ hours and then poured into a stirred 10% hydrochloric acid solution. This mixture is extracted with three 200 ml. portions of ether. The combined ether extracts are washed with 200 ml. of water, then 200 ml. of brine, dried over magnesium sulfate, and evaporated to an oil. The oil is distilled on a Kugelrohr apparatus, collecting the fraction that boils at 205°–215° C. (50 mm.) which gives 10.33 g. of 4-[[2,2-bis(p-chlorophenyl)ethyl]amino]benzoic acid, ethyl ester as an oil.

A mixture of 10.0 g. of 4-[[2,2-bis(p-chlorophenyl)ethyl]amino]benzoic acid, ethyl ester, 5.0 g. of potassium hydroxide, and 100 ml. of 95% ethanol is stirred at 80° C. for 3½ hours, cooled, diluted with 200 ml. of water, and extracted with two 150 ml. portions of ether. The combined ether extracts are washed with 100 ml. of water. The water wash is combined with the original aqueous layer and adjusted to pH 6.5 with 37% hydrochloric acid. The resulting precipitate is collected and dried in vacuo, giving 9.0 g. of the desired product as a white solid.

EXAMPLE 11

4-[[Bis(p-chlorophenyl)methyl]amino]benzoic acid, ethyl ester

To a stirred mixture of 300 mg. of lithium aluminum hydride in 25 ml. of dry tetrahydrofuran is added dropwise a mixture of 5.0 g. of 4,4'-dichlorobenzophenone in 25 ml. of tetrahydrofuran over a period of 30 minutes. A 5 ml. portion of water is added, then the solution is poured into 100 ml. of 10% sulfuric acid. The organic layer is separated and saved. The aqueous layer is extracted with two 100 ml. portions of ether. The organic phases are combined, washed with 100 ml. of water, 100 ml. of brine, dried over magnesium sulfate, and evaported, giving 4.84 g. of 4,4'-dichlorobenzhydrol.

A mixture of 1.0 g. of 4,4'-dichlorobenzhydrol, 0.8 g. of triethylamine, and 30 ml. of anhydrous ether is cooled to −15° C. A solution of 0.49 g. of methane sulfonyl chloride in ether is added dropwise. The mixture is warmed to room temperature and stirred for 30 minutes. The precipitate is collected, washed with ether, and the ether is evaporated, giving 1.47 g. of 4,4'-dichlorobenzhydromesylate.

A 25.0 g. portion of ethyl 4-aminobenzoate is dissolved in 300 ml. of anhydrous ether under nitrogen. A solution of 25.0 g. of 4,4'-dichlorobenzhydromesylate in ether is filtered directly into the solution. This mixture is stirred for 2 hours, evaporated, and the residual oil is crystallized from ethanol, giving 27.2 g. of the desired product.

EXAMPLE 12

4-[[Bis(p-chlorophenyl)methyl]amino]benzoic acid

A mixture of 13 g. of 4-[[bis(p-chlorphenyl)methyl]amino]benzoic acid, ethyl ester, 9 g. of potassium hydroxide, and 150 ml. of 95% ethanol is heated at 70° C. for 4 hours, cooled, diluted with 300 ml. of water, and adjusted to pH 6.5 with 37% hydrochloric acid. The solid is collected, dried, and crystallized from ethanol and then acetic acid, giving 5.52 g. of the desired product as yellow crystals, m.p. 245°–247° C.

No effort has been made to optimize the yields obtained in the aforementioned Examples.

We claim:

1. A compound of the formula:

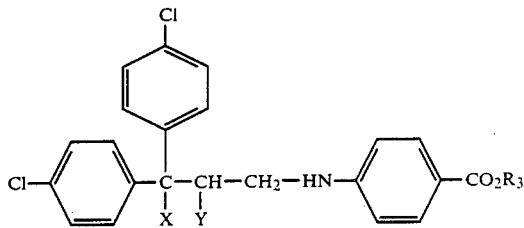

wherein X and Y are each hydrogen or taken together represent a carbon-carbon bond and $R_3$ is selected from the group consisting of hydrogen, alkyl ($C_1$–$C_4$), alkali metal and alkaline earth metal.

2. The compound according to claim 1; 4-[3,3-bis(p-chlorophenyl)propylamino]benzoic acid.

3. The compound according to claim 1; ethyl 4-[3,3-bis(p-chlorophenyl)propylamino]benzoate.

4. The compound according to claim 1; sodium 4-[3,3-bis(p-chlorophenyl)propylamino]benzoate.

5. The compound according to claim 1; 4-[3,3-bis(p-chlorophenyl)allylamino]benzoic acid.

6. The compound according to claim 1; ethyl 4-[3,3-bis(p-chlorophenyl)allylamino]benzoate.

7. The compound according to claim 1; sodium 4-[3,3-bis(p-chlorophenyl)allylamino]benzoate.

8. A method of reducing the cholesterol content of the arterial walls of a mammal in need of such treatment which comprises administering to said mammal an effective amount of a compound as recited in claim 1.

9. A method of inhibiting atherosclerotic lesion development in a mammal in need of such treatment which comprises administering to said mammal an effective amount of a compound as recited in claim 1.

10. A method of treating atherosclerosis in a mammal in need of such treatment which comprises administering to said mammal an effective amount of a compound as recited in claim 1.

11. A pharmaceutical composition which comprises an effective antiatherosclerotic amount of a compound as recited in claim 1 in association with a pharmaceutically-acceptable carrier.

* * * * *